(12) United States Patent
Heijerman et al.

(10) Patent No.: US 7,344,734 B2
(45) Date of Patent: Mar. 18, 2008

(54) POWDER FORMULATION

(75) Inventors: Hendrikus Gerardus M. Heijerman, Zoetermeer (NL); Petrus Paulus H. Le Brun, The Hague (NL); Henderik Willem Frijlink, Eelde (NL); Anne Haaije de Boer, Drachten (NL)

(73) Assignee: Rijksuniversiteit Groningen, Groningen (NL)

( * ) Notice: Subject to any disclaimer, the term of this patent is extended or adjusted under 35 U.S.C. 154(b) by 0 days.

(21) Appl. No.: 10/223,707

(22) Filed: Aug. 19, 2002

(65) Prior Publication Data

US 2003/0053960 A1   Mar. 20, 2003

Related U.S. Application Data

(63) Continuation of application No. PCT/NL01/00133, filed on Feb. 19, 2001.

(30) Foreign Application Priority Data

Feb. 17, 2000   (EP)   ............................ 00200550

(51) Int. Cl.
*A61K 9/14* (2006.01)
*A61K 9/16* (2006.01)

(52) U.S. Cl. .................... 424/489; 424/493

(58) Field of Classification Search ........ 424/489, 424/493
See application file for complete search history.

(56) References Cited

U.S. PATENT DOCUMENTS

| | | | | |
|---|---|---|---|---|
| 3,634,582 | A * | 1/1972 | Hartley et al. | ............... 424/489 |
| 5,301,666 | A * | 4/1994 | Lerk et al. | ............. 128/203.15 |
| 5,478,578 | A | 12/1995 | Arnold et al. | ............... 424/499 |
| 6,027,714 | A | 2/2000 | Trofast | ......................... 424/45 |

FOREIGN PATENT DOCUMENTS

| | | |
|---|---|---|
| DE | 1792207 | 11/1971 |
| EP | 0 876 814 | 11/1998 |
| NL | 10 08019 | 2/1999 |
| WO | WO 95/11666 | 5/1995 |
| WO | WO 96/23485 | 8/1996 |
| WO | WO 97/03649 | 2/1997 |
| WO | WO 9703649 A1 * | 2/1997 |
| WO | WO 98/20836 | 5/1998 |
| WO | WO 9820836 A1 * | 5/1998 |
| WO | WO 98/26827 | 6/1998 |
| WO | WO 9826827 A1 * | 6/1998 |
| WO | WO 00/16745 | 3/2000 |
| WO | WO 0016745 A1 * | 3/2000 |

OTHER PUBLICATIONS

R. Clark Andrew, The use of laser diffraction for the evaluation of the aerosol clouds generated by *Int. J. Pharm.*, 115;69-78 (1995).
Annapragada et al., "An analysis of the Fraunhofer Diffraction method for particle size distribution analysis and its application to aerosolized sprays," *Int. J. Pharm.*, 127:219-227 (1996).
Edwards et al., "Large Porous Particles for Pulmonary Drug Delivery," *Science*, 276:1868-1871 (1997).
Hersey, "Ordered Mixing: A New Concept in Powder Mixing Practice," *Powder Tech.*, 11:41-44 (1975).
Higham et al., "Determination of the minimum dose of lactose drug carrier that can be sensed during inhalation," *J. Clin. Pharmacol.*, 40:281-282 (1995).
Hindle et al., "Cascade impaction methods for dry powder inhalers using the high flowrate Marple-Miller Impactor," *Int. J. Pharma.*, 134:137-146 (1996).
Lacey, "The Mixing of Solid Particles," *Trans. Inst.Chem.. Engineers*, 21:53-59 (1943).
Lowry et al., "Protein Measurement with the Folin Phenol Reagent," *J. Biol. Chem.*, 193:265-275 (1951).
Olsson et al., "The use of inertial impactors to measure the fine particle dose generated by inhalers," *Pharmeuropa*, 8:291-298 (1996).
Staniforth, "Order out of chaos," *J. Pharma. Pharmacol.*, 39:329-334 (1987).
Timsina et al., "Drug delivery to the respiratiory tract using dry powder inhalers," *Int. J. Pharm.*, 101:1-13 (1994).
Travers et al., "The mixing of micronized sodium bicarbonate with sucrose crystals," *J. Pharma. Pharmac.*, 23 Suppl:260S-261S (1971).
English abstract of DE 1792207.
English abstract of NL 1008019.

* cited by examiner

*Primary Examiner*—Humera N Sheikh
(74) *Attorney, Agent, or Firm*—Banner & Witcoff, Ltd.

(57) ABSTRACT

The invention relates to a powder formulation for administration by inhalation comprising an active substance and a pharmaceutically acceptable excipient, which composition has the form of a physical mixture and comprises from 5 to 25 wt. % of the excipient, and wherein the active substance has a particle size distribution of from 0.5 to 10 μm, and wherein the excipient has a particle size distribution of from 15 to 500 μm.

8 Claims, 6 Drawing Sheets

POWDER FORMULATION

This application is a continuation of prior application No. PCT/NL01/00133, filed Feb. 19, 2001; which claims priority from European Patent Application No. 00200550.2, filed Feb. 17, 2000.

BACKGROUND OF THE INVENTION

1. Field of the Invention The invention relates to the field of pharmacy and drug formulation. The invention relates particularly to a powder formulation of a therapeutically active substance for administration to a patient by inhalation.

2. Description of the Related Art

Dry powder inhalers (DPI's) are on the market since the Spinhaler was introduced nearly 30 years ago. Basically, DPI's consist of a powder formulation, a dose (measuring) system and a disintegration principle.

The powder formulation contains a therapeutically active ingredient, typically a drug, in the required size range for effective deposition in the lower respiratory tract (target area) of the user of the inhaler. The required size range is obtained either directly from precipitation, spray drying or with comminution techniques, like jet milling (fluid energy milling) or ball milling.

Different effective particle diameters or size ranges have been described for solid drug particles for inhalation. Particles exceeding 5 µm are believed to deposit mainly in the oropharynx and the efficiencies of deposition mechanisms have been reported to confine the minimum diameter for aerosol particles to 0.5 µm. The diameters of spherical particles below which significant deposition in the head region during oral inhalation (at 60 l/min) is avoided are calculated to be 2.4 micron for particles with a density of 1.0 g/cm$^3$, respectively 1.4 micron for particles with a density of 1.5 g/cm$^3$. European Patent Application 0 876 814 claims that only particles <2 µm can reach the alveolar region.

It is difficult to compare the different studies disclosed in the art with each other, because of the different definitions used. In the early publications, recommended particle sizes often refer to geometric diameter or equivalent volume diameter ($D_e$). In more recent studies, the mass median aerodynamic diameter is often described, but sometimes this MMAD makes a correction for particle density ($\rho_p$) only, whereas MMAD (by definition) should take account of the dynamic shape factor ($\chi$) as well:

$$D_a = D_e(\rho_p/\chi)^{0.5}$$

Edwards et al. (Science 276 (1997) 1868-1871) described a new type of inhalation aerosol consisting of large particles (>5 µm, up to 20 microns) with low densities ($\rho$<0.4 g/cm$^3$), having the same aerodynamic diameters as solid particles with unit density (or higher) and much lower geometric diameters. They claim that these so-called 'large porous particles' penetrate deeply in the lungs. Because of their size they escape the lungs' natural clearance mechanisms (e.g. phagocytic clearance by macrophages in the alveoli), and increase both the bioavailability (as achieved for testosterone) and duration of the therapeutic effect from sustained release particles (as achieved for insulin) composed of biodegradable polymers. The authors also claim that large porous particles can be aerosolized from a DPI more efficiently than smaller nonporous particles, resulting in higher respirable fractions of the inhaled therapeutics. This is explained by a much higher agglomeration tendency of small, high density particles with high surface-to-volume ratio, which causes these particles to exit the DPI as small agglomerates rather than as primary entities.

Achieving a high dose reproducibility with micronized powders is impossible because of their poor flowability and extreme agglomeration tendency. To give the most effective dry powder aerosol, the particles should be large while in the inhaler, but small when discharged into the respiratory tract. Therefore, an excipient (such as lactose or glucose) is generally added either as a diluent (e.g. for preparing spherical pellets) or as an excipient (e.g. for preparing adhesive mixtures).

In adhesive mixtures, the fine drug particles are distributed homogeneously over the surface area of the large excipient crystals, held in position by mild drug-to-excipient interaction forces (e.g. van der Waals forces), that must be exceeded during inhalation by removal forces for fine particle detachment, thus, to transport only the drug particles into the lower respiratory tract. Only two exceptions are known: the Fisons Spincaps, containing pure DSCG and the ASTRA Turbuhaler, containing pure budesonide or terbutalin sulphate.

The use of substantial amounts of lactose (or glucose) in inhalation powders is arguable, however, because of possible irritation during inhalation, which may result in coughing and bronchoconstriction. Drug particles, adhering to coarse lactose crystals that are deposited in the mouth and throat, may result in local (or systemic) side effects, especially the cortico steroids. Recently, Higham et al. (Clin. Pharmacol. 40 (1995) 281-282) investigated the determination of excipient lactose from the Diskhaler by 20 healthy volunteers and found that more than fifteen volunteers (i.e. >75%) were able to sense (taste or feel) a dose of only 3 mg excipient substance. Even the inhalation of 1 mg lactose was still sensed by 8 subjects. WO 97/03649 refers to physiological benefits from introducing as little powder as possible to the lungs, especially material other than the active ingredient to be inhaled.

The desired type and size fraction of (excipient) lactose varies with specific demands regarding powder disintegration and powder flow; both being dependent on inhaler design as well. Mostly, crystalline alpha lactose monohydrate is used as excipient. Timsina et al. (Int. J. Pharm. 101 (1994) 1-13) explained that the excipient particles, usually lactose, are incorporated with the micronized drug powder to make it less cohesive and more freely flowing, thus making it easier to handle.

Several studies are known in which a positive effect from the presence of fine or micronized lactose in inhalation powders on fine particle yield from the DPI is claimed. U.S. Pat. No. 5,478,578 quotes that the inhalable active substance content is negatively affected by a coarse excipient as proposed in DE-A-1792207. In said U.S. patent it is therefore stated that the inhalable portion of the active substance in inhalation powders can be controlled within wide limits (while keeping good accuracy of metering) by combining the micronized active substance with suitable quantities of a mixture of acceptable excipients. It is disclosed that one component of the mixture has to have a mean particle size of less than 10 µm, whereas the other component has to have a mean diameter of greater than 20 µm (generally below 150 µm and preferably below 80 µm). The weight ratios of the fine and coarse excipient are to be between 1:99 and 95:5; preferably between 5:95 and 70:30 and especially between 10:90 and 50:50.

A few studies are known in which modification of the surface morphology of lactose excipient particles is described for maximal drug particle detachment from the 
excipient crystals during inhalation (e.g. International patent publications WO 95/11666, WO 96/23485 and WO 97/03649).

In WO 95/11666 it is described that the surface of an excipient particle is not smooth, but has asperities and clefts with higher surface energy. Drug particles are attracted to and adhere to these areas more strongly than on other sites of the excipient surface. As a consequence, drug particle detachment during inhalation and thus, respiratory deposition are reduced. The asperities are explained in terms of adhering fine grains. Treatment consists of gently milling the excipient particles, preferably in a ball mill at a low number of revolutions per minute (e.g. 6), for about six hours. During this treatment, asperities (small grains) are dislodged from the excipient surface and attracted to the high energy sites in clefts but the size of the excipient particles is not substantially changed. As a result of the treatment, the total number of active sites on the excipient particles is strongly reduced. The treatment may be carried out before the active particles are added or in the presence of active particles.

WO 96/23485 describes the use of small amounts of additive particles for the occupation of the active sites of excipient particles. The weight percent of the additive particles must not be too high (for most materials less than 2%) in order to avoid segregation of the mixture with the active ingredient. The additive particles are of an anti-adherent or anti-friction material (e.g. magnesium stearate, leucine, lecithin, talc, starch and silicon dioxide) or a combination of more materials. It is particular advantageous for the additive material to comprise an amino acid, because of observed high respirable drug fractions, little segregation and little amino acid being transported into the lower lung.

WO 97/03649 expands the application of additives to inhalation powders containing advantageously 70%, to most preferably 99% (by weight) of the active material. 90% (by weight) of the particles in this powder should advantageously be smaller than 63 µm and more preferably smaller than 10 µm. The additive material may be present in the powder both in the form of small particles and in the form of a coating on the surfaces of the particles of active material. It is explained that the additive material interferes with the weak bonding forces (e.g. van der Waals and Coulombic forces) between the drug particles as weak links or chain breakers, helping to keep them separated. The same substances are proposed as in WO 96/23485. Both patents describing the use of additives have been worked out in the so-called Passcal™ Technology (corrasion process) as applied by RP Scherer AG (Baar, Switzerland, 1996). The deposition of additives in the lower respiratory tract has yet unknown safety aspects however.

ASTRA DRACO for their latest formulations (e.g. with salbutamol sulfate and formoterol fumarate) use only micronized lactose as excipient (NL-A-10.08019). They described the preparation of spherical pellets, with a bulk density between 0.28 and 0.38 g/cm$^3$, containing micronized drug and a mono-, di- or polysaccharide (preferably alpha lactose monohydrate), both in size fractions <10 μm (preferably 1-7 μm), in order to reduce dose variation. The use of micronized lactose is preferred to much coarser lactose crystals because of a much better dispersion of the drug, observed during in vitro testing of the formulations. Pellet size is in the range 100-2000 μm (preferably between 100 and 800 μm.

Typically, DPI's, contain a dose system, which contains the powder formulation either in bulk supply or quantified into individual doses stored in unit dose compartments, like hard gelatin capsules or blisters. Bulk containers are equipped with a measuring system operated by the patient in order to isolate a single dose from the powder immediately before inhalation. High dose reproducibility requires excellent content uniformity and reproducible dose weighing of the powder into the dose system as well as complete discharge of this dose system by the inspiratory air during inhalation. Flow properties of the powder formulation, and long term physical and mechanical stability in this respect, are more critical for bulk containers than they are for single unit dose compartments. Good moisture protection can be achieved more easily for unit dose compartments (like blisters), however.

The disintegration principle of the DPI generates primary drug particles or small agglomerates from the powder formulation during inhalation by disrupting spherical pellets or detaching small drug particles from the much larger excipient crystals. The amount of fine drug entities discharged from the inhaler's mouthpiece during inhalation is largely dependent on the interparticulate forces in the powder formulation (between drug and drug particles or between drug and excipient particles) and the efficiency of the disintegration principle of the DPI to utilize the energy from the inspiratory air stream (at a given flow rate). Most of the presently marketed DPI's containing adhesive mixtures, deliver a maximal fine particle fraction of 20-25% of the nominal dose. DPI's with spherical pellets have higher fine particle outputs, up to a maximum of 40-50% of the nominal dose (above approx. 40-50 l/min for the Turbuhaler and 120 l/min for the Spinhaler).

In U.S. Pat. No. 5,301,666, a specific DPI for use by asthma patients has been disclosed. This DPI comprises a cyclone chamber. The particles of active substance which the asthma patient inhales contain virtually no larger-sized constituents or particles. 90-95% of the particles released are of respirable size.

SUMMARY OF THE INVENTION

Many micronized powders of active ingredients for inhalers form (natural) agglomerates as a consequence of their cohesive nature. Upon inhalation, a dose of the powder is discharged as a big lump of powder, or several smaller clusters of particles from the dose delivery system and conveyed by the inspiratory air to the patient's respiratory tract. Inhalation of these agglomerates or clusters is not advantageous from a viewpoint of efficiency of administration and may even cause discomfort to the patient. As mentioned above, in order to maintain a good flowability of the powder and in order to prevent said agglomerates or clusters from being inhaled, a certain amount of an excipient material is often necessary.

The present invention provides a specific powder composition for administration by inhalation. In particular, the invention relates to a powder formulation for administration by inhalation comprising an active substance and a pharmaceutically acceptable excipient, which composition has the form of a physical mixture and comprises from 5 to 25 wt. % of the excipient, and wherein the active substance has a particle size distribution of from 0.5 to 10 μm, and wherein the excipient has a particle size distribution of from 15 to 500 μm.

BRIEF DESCRIPTION OF THE DRAWINGS

FIG. 1 schematically depicts a cross-sectional view of a dry powder inhaler.

FIG. 2 schematically depicts an exploded view of the inhaler of FIG. 1, indicating the flow path of the powder during inhalation.

DETAILED DESCRIPTION OF THE INVENTION

The present powder formulation is specifically suitable for use in a dry powder inhaler as described in the above mentioned U.S. Pat. No. 5,301,666. When used in said inhaler, it has been found that hardly, if any, of the excipient enters the respiratory tract of the patient. Accordingly, a considerable source of discomfort in patients dependent on this type of drug administration is substantially eliminated. The patient will not be burdened with the discomfort of an excess of powder in the mouth and throat and reactions like cough may be avoided.

Typically, due to cohesive forces, the active substance will form natural agglomerates. During inhalation, a dose of the powder formulation is discharged from the dose system as a big lump of powder, or several smaller clusters of particles and conveyed by the inspiratory air towards the cyclone chamber. Inside this chamber, the agglomerates (including excipient particles) rotate by the action of centrifugal forces, unless they are (or become) so small that the drag force exceeds the centrifugal force, and the particles are transported by the air into the patient's respiratory tract. The cyclone has a much higher disintegration efficiency, particularly when used in combination with the present powder formulation, than the disintegration principle of other DPI's. This is at least partly due to the continuation of particle break-up during inhalation. Most other DPI's discharge a dose of powder formulation more or less instantaneously and therefore utilization of the energy of the inspiratory air is rather incomplete.

Furthermore, it has been found that the particles of the excipient material having the specific characteristics required by the invention act as a sweeper and remove adhering fines of the active substance by impact and shear forces in the inhaler from surfaces of the disintegration chamber to which they may have adhered. Consequently, the efficiency of the inhaler is significantly improved.

The present powder formulation has the form of a physical mixture. In this respect, the formulation is distinct from the above described adhesive mixtures wherein the active substance is bound to the excipient by mild interaction forces. In accordance with the invention, a physical mixture is characterized in that interactive forces between the components of the mixture are substantially absent. In other words, the active substance and the excipient are substantially chemically and physically inert towards each other.

The distinction between adhesive and physical mixtures is an important aspect of the invention. Therefore, the following historical discussion of these two types of mixtures is included.

Powder mixing is a statistical process leading, in most cases, to a random arrangement of the particles in the powder. The scientific basis of random mixing theory has been established midway of the previous century. Several equations were developed for homogeneity assessment of (binary) dry powder mixtures, that exist of particles being identical in every respect, except color (e.g. P.M.C. Lacey, Trans. Inst. Chem. Engineers 21 (1943) 53-59). A crucial assumption for random mixing is that particles are non-cohesive and non-interacting. Staniforth (1987) resisted this assumption and claimed that in fact, particles are always interacting. Whether this results in particle-to-particle association in a mixture or not, depends on the order of magnitude of other forces, like the force of gravity, which is governed by the particle dimension (mass). In most random mixtures, particles are different in size, mass and shape, which bears the hazard of segregation.

Already in 1971 (D. N. Travers, R. C. White, J. Pharm. Pharmac. 23 Suppl. (1971) 260S-261S) described the adsorption of fine particles onto much larger 'host' crystals in their mixtures. Mixtures of this type, often exhibit a higher degree of uniformity than can be assessed on the basis of homogeneity equations for random mixtures. This was reason for Hersey (Powder Technol., 11 (1975) 41-44) to develop a 'disorder to order' concept for this newly distinguished type of cohesive particulate systems, termed 'ordered mixing'. The term ordered for indicating a type of mixture was rejected in the following decade, and it became popular to describe the two types of mixtures as 'non-interactive'(random) and 'interactive' (ordered). Staniforth (J. Pharm. Pharmacol., 39 (1987) 329-334) provided arguments against this nomenclature in 1987 and recommended to speak rather in terms of 'adhesive' (cohesive) and 'non-adhesive' (non-cohesive) in order to distinguish between both different mixture types. In addition, it has become habitual practice to use the term 'ordered' (higher than theoretically possible) and 'random' only when referring to the degree of homogeneity.

The above mentioned arguments and recommendations have been adopted in this text. Consequently, common mixtures of fine drug particles and coarser carrier particles for inhalation, in which the drug particles are homogeneously distributed over the surface of the carrier particles and attached to these carrier particles by mild interaction forces (e.g. van der Waals forces) are termed adhesive mixtures.

Mixtures of fine drug particles with coarse excipient particles in which this interaction between drug and excipient is not demonstrable, are random mixtures according to the former, and non-adhesive mixtures according to the present nomenclature. However, the term non-adhesive may be confusing for the type of mixture described in this patent, because there is some cohesion between the micronized drug particles, notwithstanding the absence of noticeable adhesion between drug and excipient particles. For this reason, the non-adhesive type of formulation in this text is referred to as a physical mixture (which used to be a synonym for random mixture in its former meaning).

The active substance on which the present powder formulation is based may in principle be any type of active substance which is intended for administration by inhalation. Typical examples include drugs used for pulmonary indications, such as beta-agonists, anti-cholinergics or corticosteroids, antibiotics, and therapeutically active peptides or proteins. The choice for the active substance is not limited to drugs administered to obtain local effects, but also comprises those drugs that are administered to obtain systemic effects. In the latter case, the lung is employed as an absorption organ, and the therapeutic target is thus not limited to pulmonary diseases but may also relate to other indications like rheumatic diseases, cystic fibrosis, cancer or diabetes.

In a preferred embodiment, the active substance is colistin. Colistin is a drug that is currently used as antibiotic drug for treatment of cystic fibrosis patients. Cystic fibrosis (CF) is a failure in humans of a cAMP regulation of chloride transport, known to be inherited in an autosomal recessive pattern, and located on chromosome 7. At present, CF patients in The Netherlands rely on a nebulizer for the inhalation of antibiotic drugs such as Tobramycin or Colistin. Treatments in order to delay or prevent chronic infections with colistin include inhalation of a dose of 160 mg twice a day from an aqueous solution. It has been found that a powder formulation consisting of colistin and lactose, in particular crystalline alpha lactose monohydrate, benefits greatly from the specific characteristics of the powder formulation and the sweeper effect mentioned above.

The active substance has a particle size distribution of from 0.5 to 10 µm, preferably from 1 to 5 µm. This specific particle size distribution, particularly in combination with the formulation and disclosed inhaling device, ensures that substantially no active substance remains behind in the cyclone chamber of the DPI. Even more important is the fact that this particle size distribution ensures an effective deposition of the active substance in the target area. In accordance with the invention, the term particle size distribution is defined as to indicate that at least 50 wt. %, preferably at least 75 wt. %, of the specific component has a size within the specified range. The particle size distribution of the discharged particles may for instance be determined by a laser diffraction technique, or cascade impactor analysis. These techniques are disclosed in inter alia Hindle et al., Int. J. Pharm., 134 (1996), 137-146, Olsson et al., Pharmeuropa, 8(1996), 291-298, Clark, Int. J. Pharm., 115 (1995), 69-78, and Annapragada et al., Int. J. Pharm., 127 (1996), 219-227.

Preferably, the powder formulation contains only the active substance and the pharmaceutically acceptable excipient, and no other additives. In addition, it is preferred that the formulation comprises as much of the active substance as possible. In order to achieve the desired effect of the excipient, said excipient will typically be present in an amount of from 5 to 25 wt. %, preferably below 20 wt. %, based on the weight of the formulation.

The excipient is a pharmaceutically and toxicologically acceptable substance and could also be referred to as carrier. Although the chance of any of the excipient entering the respiratory tract during inhalation is virtually nil when using a DPI based on a cyclone mechanism, it is recommendable to avoid any risk of adverse side-reactions, irritation, inflammation or even infection should nevertheless a minute amount of the excipient be inhaled.

The excipient is to be chosen such that it forms a physical mixture with the active substance, rather than an adhesive mixture. It is a major advantage of the invention that the absence of an interaction between the active substance and excipient makes the surface properties of the excipient less critical. In principle, the skilled person will be able to select a suitable excipient material based on his general knowledge of the field. Examples of suitable materials include mono- and disaccharides, such as lactose or glucose, and polysaccharides. Particularly good results have been obtained using crystalline alpha lactose monohydrate as an excipient material.

The excipient has a particle size distribution chosen such that the particles are larger than the effective cut-off diameter of the cyclone, which depends primarily on the flow rate and the dimensions of the cyclone chamber, and secondarily on the aerodynamic particle properties (shape and density). Typically, it is preferred that the excipient's particle size distribution has a lower limit of at least 15 µm, more preferably at least 25 µm. The upper limit of the particle size distribution of the excipient will mostly be determined by the dimensions of the dose compartment in the DPI. Compared to those dimensions the particles should be relatively small. Further, the particles should not be so large that segregation of the physical mixture and disturbance of the flow pattern inside the cyclone chamber may occur. It is further to be noted that variations in weighed powder quantities, e.g. in the dose compartments, will increase with increasing excipient particle size. Accordingly, the excipient has a particle size distribution below 500 µm.

The powder formulation may be prepared in any conventional manner for preparing physical mixtures. One suitable way comprises mixing the active substance with the excipient in a tumbling mixer.

The powder formulation is particularly adjusted for administration using a dry powder inhaler which contains the powder formulation in preloaded cartridges of compartments, e.g. bores in a cylindrical disk. The amount of powder formulation in each compartment is within a range (preferably 10-25 mg) that is acceptable to the patient for a single inhalation (with respect to irritation, like cough) and does not overload the cyclone. The number of bores per disk (number of inhalations) is preferably sufficient for one treatment. The compartment disk allows forced filling, e.g. by scraper techniques. The inhaler has a cyclone based disintegration chamber in which the active substance agglomerates and large excipient particles circulate by the action of centrifugal force. Only smaller particles that have been detached from the agglomerates can be discharged by the inhaled air and enter the user's respiratory tract. The mouthpiece adds some false air (sheath flow) to the powder aerosol, thereby reducing both the total air flow resistance of the inhaler and the deposition of the active substance in the mouth.

The invention will be elucidated further with reference to a drawing of a dry powder inhaler.

Figure 1:
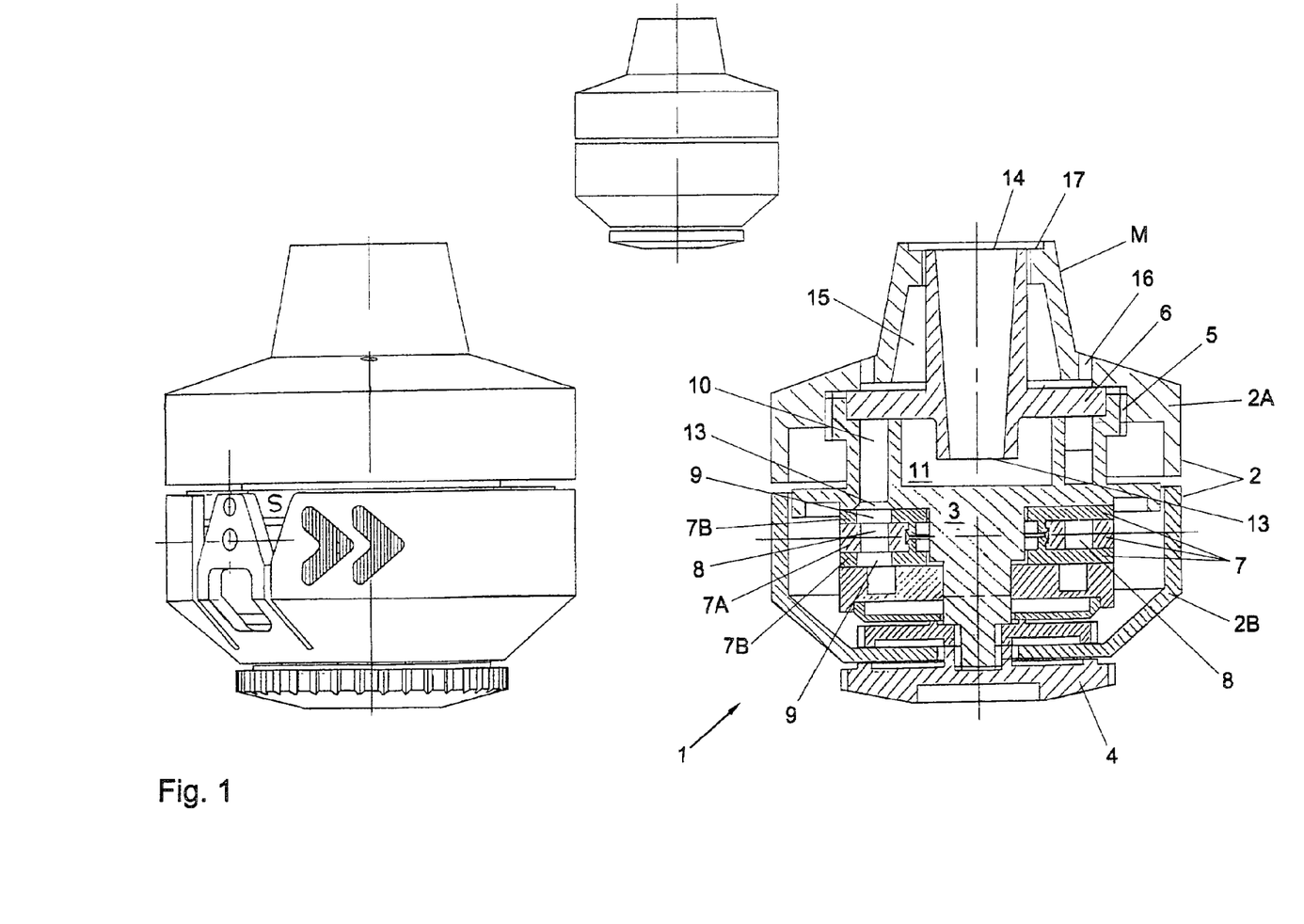
Figure 2:
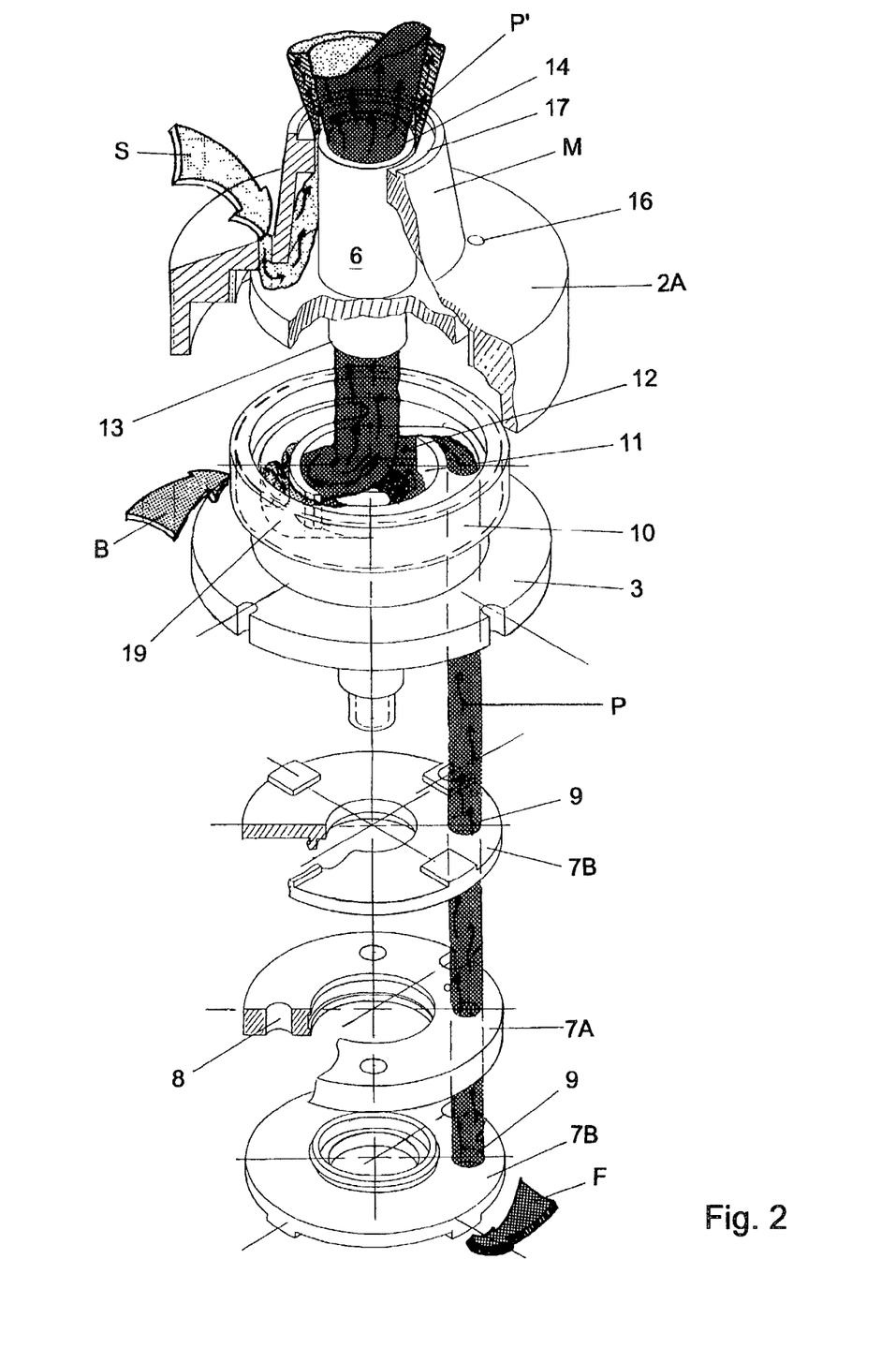
Figure 3:
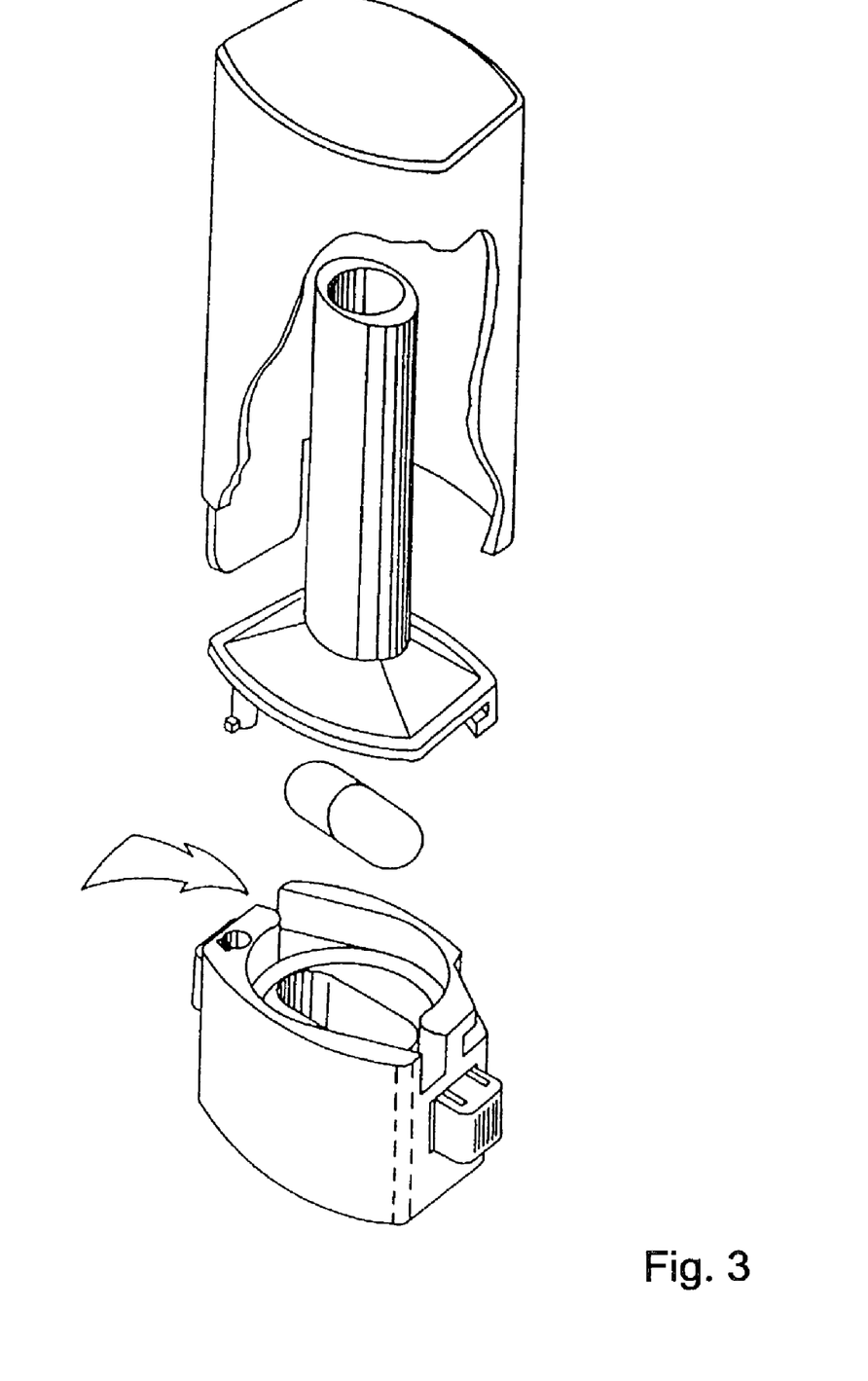
FIG. 3 schematically deolcts a commercially available commercial inhaler, the Pharmachemic Cyclohaler.

In the drawings is:

FIG. 1 a cross-sectional view of the inhaler;

FIG. 2 an exploded view of a part of the inhaler of FIG. 1, indicating the flow path of the powder during inhalation; and FIG. 3 shows a commercially available inhaler, viz. the Pharmachemie Cyclohaler which equals the ISF Inhaler and the Novartis Foradil Inhaler.

The drawings serve only to show a schematical representation of a currently preferred embodiment of the inhaler. It shall be clear that a dry powder according to the invention can be inhaled using inhalers of many types and designs, which are in practice variants of the inhaler shown in the appended drawings. In the drawings, identical or corresponding parts have been designated with the same reference numerals.

Referring to FIGS. 1 and 2, the inhaler 1 comprises an outer housing 2 having a top portion 2A and a bottom portion 2B. The inhaler 1 further comprises an inner housing 3. The bottom portion 2B of the outer housing 2 is connected to the inner housing 3 by means of a screw 4, while the top portion 2A of the outer housing 2 is directly screwed onto the inner housing 3 by means of screw thread 5, such that a cyclone chamber outlet 6 is interposed. The screw 4 preferably comprises an air inlet opening. The top portion 2A of the housing 2 comprises a mouthpiece M surrounding the cyclone chamber outlet 6.

The inner housing 3 carries a dose compartment disk 7. The dose compartment disk 7 comprises a central disk 7A, the bottom and top portions of which are provided with cover plates 7B.

The central disk 7A is provided with a number of powder compartments 8. The powder compartments 8 are embodied as cylindrical bores which can each be axially aligned with a corresponding opening 9 in the cover plates 7B, such that a channel is formed from which the powder contained in the aligned powder compartment 8 can be entrained with an air flow F passing through the channel.

The air flow F is generated by inhalation through the mouthpiece M. Upon inhalation ambient air enters the space between the bottom portion 2B of the outer housing 2 and the inner housing 3, thus forming the air flow F entering the channel through opening 9 in the lower cover plate 7B.

The inner housing 3 comprises a further channel 10 for guiding a powder flow P, i.e. the air flow F comprising the entrained powder, towards a cyclone chamber 11. The further channel 10 is an entry side axially aligned with the opening 9 of the upper cover plate 7B. The further channel 10 comprises an exit side 12 which is disposed such that the powder flow P can enter the cyclone chamber 11 tangially.

The cyclone chamber 11 is connected to the cyclone chamber outlet 6 which preferably forms a diverging channel extending from a channel entry 13 to a channel exit 14.

As discussed above, the cyclone action of the cyclone chamber 11 and the cyclone chamber exit 6 provide for a separation of the particles of the physical powder mixture, such that the small active substance particles exit the channel 14 in a powder flow P', while the large excipient particles remain, at least for a substantial portion, in the cyclone chamber 11 or the cyclone chamber outlet 6 during inhalation.

To facilitate inhalation, a cyclone bypass flow B can be provided that enters the space between the top and bottom portions 2A and 2B of the housing 2, and that flows through a bypass channel (not shown) to the cyclone chamber 11 to enter it tangentially.

The separated powder flow P' is upon exit of the cyclone chamber 6 surrounded by a sheath flow S of ambient air. The sheath flow S enters an annular channel 15 that extends co-axially with the cyclone chamber outlet 6 through sheath flow orifices 16. The sheath flow S exits the channel near the tip 17 of the mouthpiece M.

After the powder compartment 8 has been relieved of its contents in one or more inhalations, the bottom portion 2B of the housing can be indexed relative to its top portion 2A around rotational axis A using screw 4 under entrainment of the central disk 7A, such that a new powder compartment 8 is axially allied with the openings 9 and the entry of the further channel 10.

After inhalation, the excipient particles of the physical mixture remain in the cyclone chamber 11. The cyclone chamber 11 can be emptied by disassembling the inhaler 1 e.g. when installing a new dose compartment disk 7.

The invention will now be further elucidated by the following, non-restrictive example.

EXAMPLE

A lactose size fraction of 106-150 µm, derived from 100 M lactose (DMV International, Veghel, The Netherlands) was used as excipient. The fraction was prepared by subsequent vibratory sieving (20 minutes in a Fritsch Analysette 3, Idar-Oberstein, Germany) and air jet sieving (10 minutes in an Alpine A200, Augsburg, Germany) of small quantities (approx. 50 g) of the starting material. Micronized Colistin was prepared by fluid energy milling (GfM, Hamburg, Germany), but because the size distribution of the active ingredient was not satisfactory, size reduction of the crystalline material was continued for 26.5 hours in a ball mill (50 g in a container of 750 ml, filled with ceramic balls of different sizes to a filling degree of 67%). The container was placed on a home constructed drive. Size distributions before and after milling in the ball mill were measured with laser diffraction technique (Fraunhofer theory, using Sympatec HELOS Compact, model KA with 100 mm lens) using dry dispersion with a RODOS disperser at 4 bar.

A physical mixture of 83.3% (w/w) of the micronized Colistin and 16.7% (w/w) of the lactose fraction 106-150 micron, in a batch size of 10 g, was prepared in a special stainless steel mixing vessel of 160 ml, using a tumbling mixer (Turbula T2C, WA Bachofen, Basel, Switzerland). Total mixing time was 10 minutes at 90 rpm. Mixing was performed under ambient atmospheric conditions; the mixture was stored in a small glass container in the dark.

Inhalation experiments with the mixture were performed at 60 l/min with a test inhaler (see FIG. 1), having the same disintegration principle (cyclone) as the Colistin dry powder inhaler (prototype). Small amounts (doses) of 12 mg (containing 10 mg of Colistin and 2 mg of the lactose fraction) were weighed and manually inserted in the powder channel. One test series included six subsequent inhalations of 12 mg (total dose of 72 mg).

The aerosol cloud from the inhaler was characterized with a laser diffraction technique (Sympatec HELOS Compact, model KA with 100 mm lens) using the Fraunhofer theory. A special inhaler adapter was used in order to adjust the required flow rate through the inhaler device. The adapter consisted of a cylindrical chamber with side tubes connecting the adapter at both sides to the housing of the laser diffraction apparatus. The inhaler device was connected to the front of the adapter, whereas the vacuum system was connected to the rear end of the adapter. Thus, a closed system was created through which the flow rate can be controlled very carefully and in which the aerosol cloud passes the laser beam for the measurement. Standard HELOS software was used: start and stop of the measurement was triggered on channel 32 with 0.1% difference in optical signal (compared with the signal during reference measurement). The mass fraction of the dose delivered by the inhaler was not analyzed during these experiments (no particle collector in line with the adapter).

In addition to these laser diffraction experiments at 60 l/min with the 83.3% Colistin formulation, the following tests were performed:

I The aerosol cloud from the physical mixture with 83.3% of Colistin as released by the test inhaler at 60 l/min was also characterized with a cascade impactor. The inhalation time was 3 s. For each duplicate measurement, 6 doses of 12 mg were inhaled. A four stage glass impactor of the Fisons type was used (Elgebe, Leek, The Netherlands) with dry bent inlet tube and 20 ml of solvent (pure water) on the impactor stages. The theoretical cut-off diameter of the second stage of this impactor at 60 l/min is 8.74 µm for particles with a true density of 1.5 g/cm$^3$. For the analysis of Colistin retained from the different impactor stages, a technique for protein measurement described by Lowry et al., J. Biol. Chemistry 193 (1951), 265-275 was applied.

II The physical mixture with 83.3% Colistin was also tested with the test inhaler at 20, 30, 40 and 50 l/min. The aerosol cloud was characterized with laser diffraction technique, using the procedures as described previously. At each flow rate (inhalation time 3 seconds), 6 subsequent inhalations of 12 mg were performed.

III The amount of lactose excipient in the physical mixture was varied. Mixtures with 25 50, 75 and 100% micronized Colistin (of the same particle size distribution) were prepared, using the same mixing procedures. For these mixtures, a finer lactose fraction of 63-106 μm was used in order the test additionally the effect excipient coarseness on the dispersibilty of the formulation. All mixtures were tested with the test inhaler at 60 l/min (3s) and the aerosol clouds were characterized with laser diffraction technique. For these experiments, the amount of mixture per inhalation was 20 mg instead of 12 mg. Six subsequent inhalations per mixture completed a series.

Pure micronized Colistin was also inhaled with a commercial DPI (Pharmachemie Cyclohaler equals ISF Inhaler equals Novartis Foradil Inhaler, see FIG. 3), using the same (laser diffraction) procedures. Six hard gelatin capsules (no. 3) were filled with 10 mg per capsule and the capsules were sealed before use. Inhalation time was 3 seconds. In contrast with the test inhaler, the disintegration of the powder formulation by the Cyclohaler is not influenced by the presence of a certain amount of coarse lactose particles. Due to the high dose level (10 mg), lactose is not required as a filler excipient either.

Results and Discussion

Figure 4:
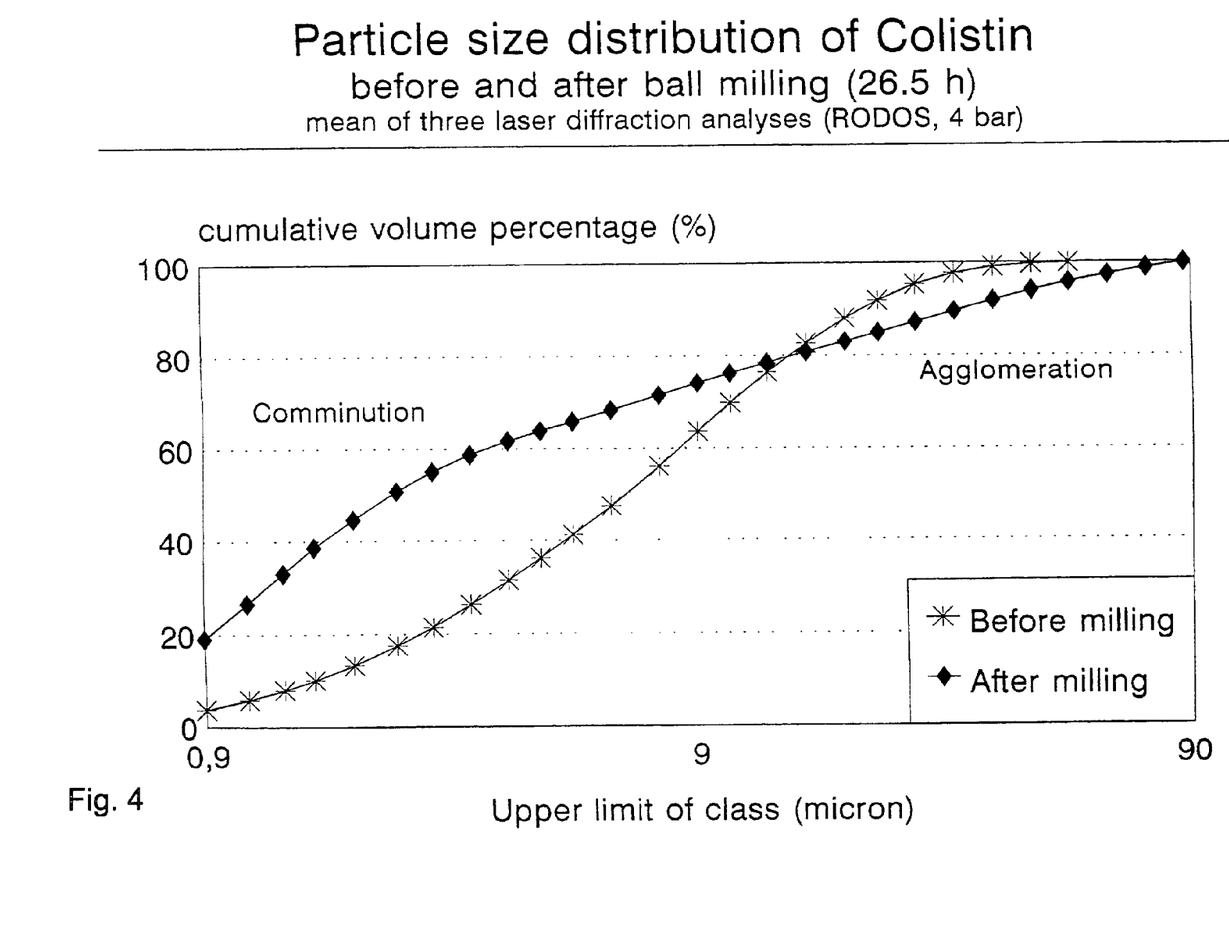
FIG. 4 graphically depicts the size distributions of Colistin before and after size reduction in the ball mill obtained from dry laser diffraction analysis (RODOS dispersion).

The size distributions of Colistin before and after size reduction in the ball mill obtained from dry laser diffraction analysis (RODOS dispersion) are presented in FIG. 4. As a consequence of this comminution, the mean diameter (X50-value) decreased from 6.43 μm to 2.14 μm (n=3), whereas the X100-value increased from 51.0 μm to 87.0 μm. The increase of the upper limit of the size distribution is the result of a minor particle agglomeration (broadening of a size distribution in a ball mill is a well known fact).

Figure 5:
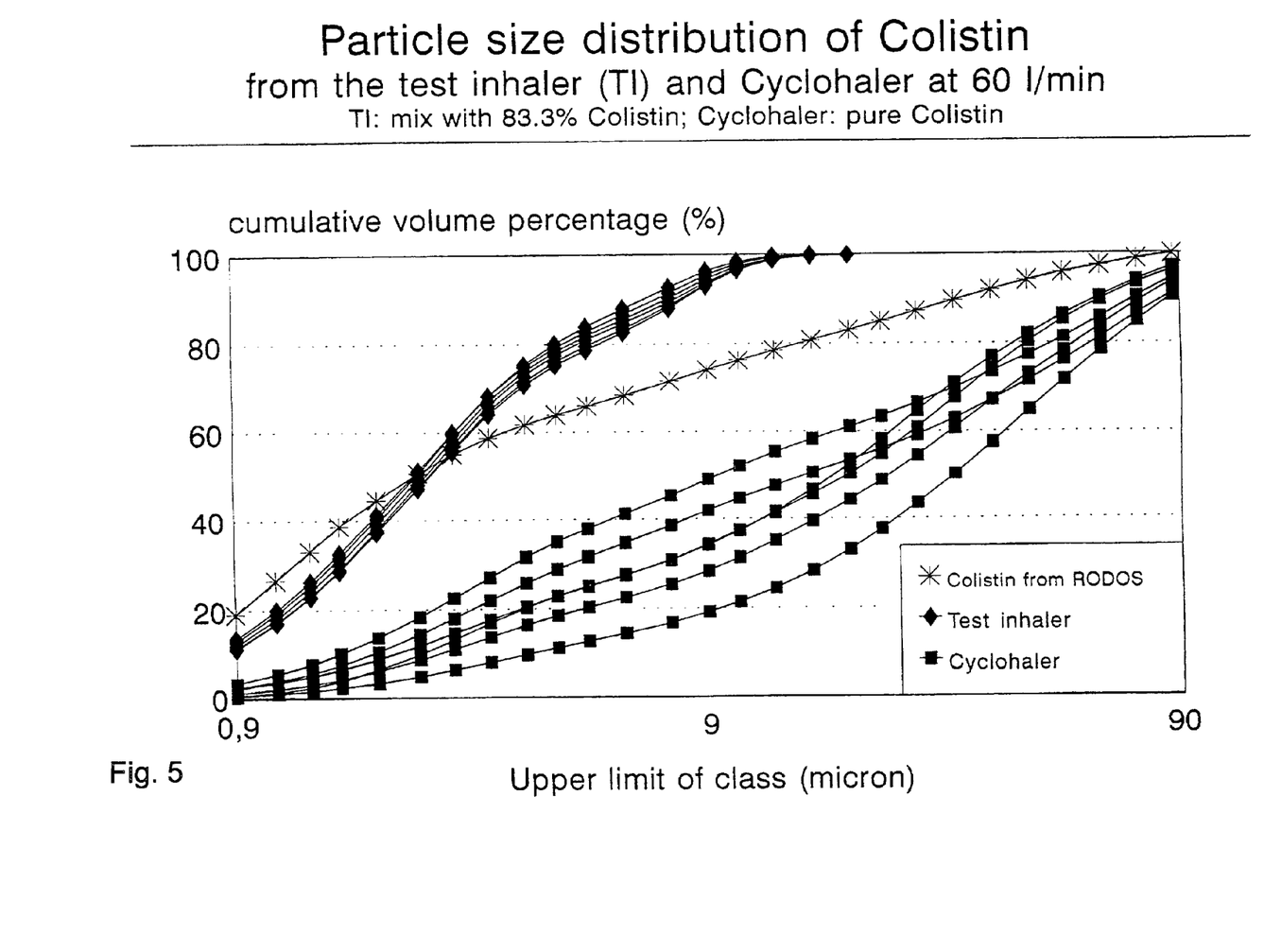
FIG. 5 graphically depicts the size distributions of the aerosol clouds from the test inhaler (for the physical mixture with 83.3% Colistin) and the Cyclohaler (for pure Colistin at 60 l/min obtained from laser diffraction analysis.

The size distributions of the aerosol clouds from the test inhaler (for the physical mixture with 83.3% Colistin) and the Cyclohaler (for pure Colistin) at 60 l/min obtained from laser diffraction analysis are presented in FIG. 5. For comparison, also the cumulative volume undersize curve for the pure Colistin (from RODOS dispersion) is depicted. The curves for all six inhalations per dose are shown for both inhalers. The difference between the marketed inhaler (ISF/Cyclohaler) and the test inhaler is extreme. The average median diameter for the aerosol cloud from the ISF-inhaler is 18.23 micron versus 2.14 μm for the primary particles of the drug from RODOS dispersion, respectively 2.24 μm for the particles in the cloud from the test inhaler. The spread between the individual inhalations for both inhalers is rather caused by an increase in X50-value with the number of inhalations performed than by a random variation, probably as a result of triboelectrification. The effect is greater for the plastic ISF inhaler than for the metal test inhaler. Remarkable is the much lower X100-value for the aerosol cloud from the test inhaler compared with the primary Colistin particles. The reason is the withdrawal of large Colistin particles as well as the lactose crystals by the cyclone during inhalation. The cut-off diameter for Colistin at 60 l/min is approximately the same as that for lactose crystals: 15 μm (very little deposition of Colistin particles in the mouth and throat).

The results from cascade impactor analysis prove that the dry powder formulation seems to fulfill the aim of 30-40% deposition efficiency in the target area. On average 38.24 mass percent (34.14 and 42.33 for the duplicate experiments) of the dose was retained from the 3rd+4th impactor stages (fraction <8,7 μm), whereas the mean deposition on stage 1 was only 7.1% (7.89 and 6.36%). The inhaler accumulations were quite low: <12.4%. All percentages are expressed in the real (total) dose. Lactose excipient withdrawal during cascade impactor analysis appeared to be nearly 100%.

The mass fraction on the3rd+4th stage (38.2%) may seem quite low compared to what is suggested by the cumulative undersize curve (from laser diffraction analysis) for the aerosol cloud from the test inhaler at 60 l/min (FIG. 5): on average nearly 94% of the delivered dose is smaller than the cut-off diameter (8.74 μm) for the second impactor stage. It must be realized however, that the delivered dose is only 67.5% of the weighed dose, because 20% is withdrawn (by the cyclone) from discharge into the impactor as coarse Colistin particles and 12.4% of the fine particles is lost by inhaler accumulation. Also, 25% of the dose (mainly as fine particles) is deposited in the inlet tube to the impactor and a few percent may be deposited as undersize particles on the first and second impactor stages. If the size distribution of the primary Colistin particles (by jet milling instead of ball milling) is improved (to 100% <15 μm), an even higher 3rd+4th stage fraction may be expected (because no coarse particles will be retained from the cyclone and thus, the delivered dose will be increased considerably).

The effect of the amount of lactose excipient in the mixture appeared to be nearly negligible, as shown in Table 1 for the X50- and X90-values derived from the cumulative undersize curves. Within the range of mixtures with 25 to 75% lactose, no significant difference between the size distributions of the aerosol clouds from the test inhaler was obtained (at 60 l/min: mean of 6 inhalations). Only the pure Colistin yielded a somewhat higher X-50 and X-90 value. The cyclone accumulation for pure Colistin was higher than for the mixtures with lactose as a result of the absence of sweeper crystals: 32-45% of the dose was retained from the cyclone (range for six inhalations), but an important contribution to this percentage is from large Colistin particles exceeding the cut-off diameter of the cyclone (at least 20%). Particles withdrawn by the cyclone could easily be tapped out after inhalation, suggesting that the triboelectrification was not extreme (although relative humidity of the air was only 30-35% during the experiments).

Figure 6:
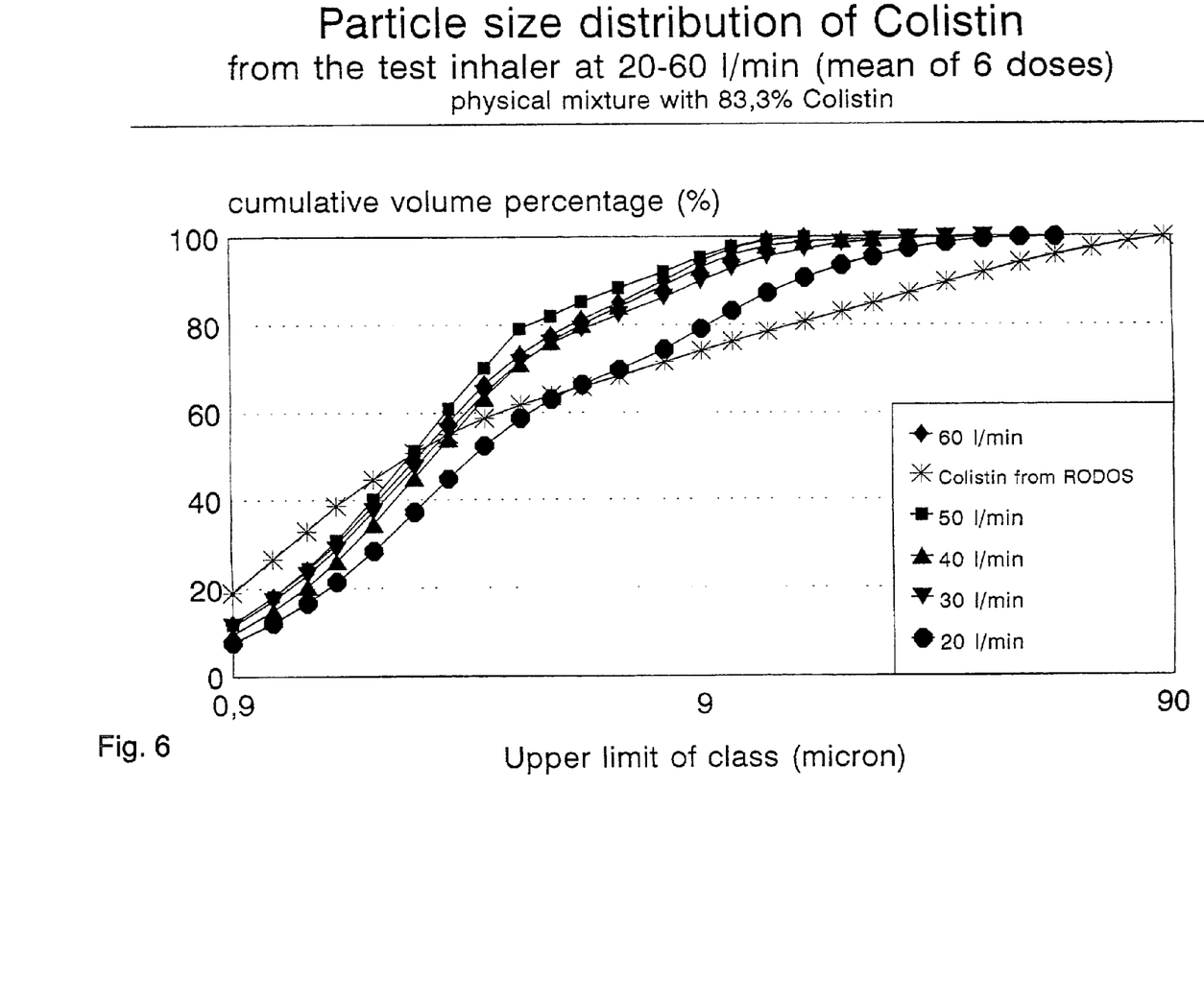
FIG. 6 graphically depicts the effect of inspiratory flow rate on the particle size distribution of the aerosol cloud from the test inhaler for the physical mixture with 83.3% Colistin (lactose fraction 106-150 μm).

FIG. 6 shows the effect of inspiratory flow rate on the particle size distribution of the aerosol cloud from the test inhaler for the physical mixture with 83.3% Colistin (lactose fraction 106-150 μm). The size distributions at all flow rates were more or less the same. X50-value ranged from 2.15 μm at 50 l/min (lowest value) to 2.43 μm at 40 l/min (highest value), except for the experiments conducted at 20 l/min when average X50-value was 3.10 micron. This somewhat higher mean X50-value obtained at the lowest flow rate is again the results of an increasing X50-value with increasing number of inhalations increase (possibly as a consequence of triboelectrification) was observed at all flow rates, but the effect was strongest at 20 l/min: at 60 l/min the 50-value increased from 2.14 μm for the first inhalation to 2.32 μm (8,4%) for the sixth inhalation; at 20 l/min the increase was from 2.24 μm to 4.25 μm (89.7%). Therefore, the disintegration, without triboelectrification, seems to be independent of flow rate between 20 and 60 l/min.

TABLE 1

| Percentage lactose in the mixture | X-50 (μm) From cum. undersize curve | X-90 (μm) From cum. Undersize curve |
|---|---|---|
| 0 | 2.3 | 7.5 |
| 25 | 2.1 | 5.4 |
| 50 | 1.9 | 4.6 |
| 75 | 2.1 | 5.0 |
| Colistin from RODOS | 2.1 | 31.0 |

Conclusions

The Colistin dry powder inhaler fulfills the aims with respect to released fine particle dose. Nearly 40% of the dose is deposited on the 3rd+4th stage of a Fisons impactor at 60 l/min, and it may be expected that this percentage can be further increased by optimizing the primary particle size distribution of the drug. The performance of the inhaler is independent of the amount and size range of the lactose fraction and the particle size distribution of the aerosol cloud is also good at flow rates below 60 l/min. No, to only a minor amount of lactose is inhaled by the patient and patient's comfort is increased considerably compared with Colistin nebulization. It is very likely to expect that patient's compliance and the quality of the therapy will benefit from this increased in comfort.

The invention claimed is:

1. Powder formulation for administration by inhalation comprising a non-adhesive, physical mixture consisting essentially of an active substance selected from the group consisting of colistin and tobramycin and a pharmaceutically acceptable excipient selected from the group consisting of monosaccharides, disaccharides and polysaceharides, wherein adhesive forces between the active substance and the excipient are substantially absent, and wherein the excipient is present in an amount between from 5 to 20 wt. % of the physical mixture, the active substance has a particle size distribution of from 0.5 to 10 μm, and the excipient has a particle size distribution of from 15 to 500 μm.

2. Powder formulation according to claim 1, wherein the active substance has an aerodynamic particle size distribution of from 1 to 5 μm.

3. Powder formulation according to claim 1, wherein the excipient has a particle size distribution of from 25 μm to 200 μm.

4. Powder formulation according to claim 1, wherein the excipient is selected from the group consisting of glucose and lactose.

5. Powder formulation according to claim 4, wherein the excipient is crystalline alpha lactose monohydrate.

6. Dry powder inhaler having a cyclone chamber operatively connected to a dosage compartment containing a powder formulation comprising an active substance selected from the group consisting of colistin and tobramycin and a pharmaceutically acceptable excipient selected from the group consisting of monosaccharides, disaccharides and polysaccharides, wherein the active substance and excipient are in the form of a non-adhesive, physical mixture, wherein adhesive forces between the active substance and the excipient are substantially absent, and wherein the formulation comprises from 5 to 20 wt. % of the excipient, the active substance has a particle size distribution of from 0.5 to 10 μm, and the excipient has a particle size distribution of from 15 to 500 μm.

7. Dosage cartridge for use in a dry powder inhaler having a cyclone chamber operatively connected to a dosage compartment containing a powder formulation comprising an active substance selected from the group consisting of colistin and tobramycin and a pharmaceutically acceptable excipient selected from the group consisting of monosaccharides, disaccharides and polysaccharides, wherein the active substance and excipient are in the form of a non-adhesive, physical mixture, wherein adhesive forces between the active substance and the excipient are substantially absent, and wherein the formulation comprises from 5 to 20 wt. % of the excipient, the active substance has a particle size distribution of from 0.5 to 10 μm, and the excipient has a particle size distribution of from 15 to 500 μm, wherein the dosage cartridge includes one or more dosage units of the powder formulation.

8. A method of delivering an active substance comprising:
a) providing a dry powder inhaler containing a powder formulation according to claim 6; and
b) delivering the active ingredient to an individual.

* * * * *